(12) United States Patent
Ishii et al.

(10) Patent No.: US 10,542,950 B2
(45) Date of Patent: Jan. 28, 2020

(54) MEDICAL IMAGE DIAGNOSTIC APPARATUS, MEDICAL IMAGE PROCESSING APPARATUS AND NON-TRANSITORY COMPUTER READABLE MEDIUM ON WHICH MEDICAL IMAGE PROCESSING PROGRAM HAS BEEN STORED

(71) Applicant: CANON MEDICAL SYSTEMS CORPORATION, Otawara-Shi (JP)

(72) Inventors: Hideaki Ishii, Nasushiobara (JP); Yasuyuki Miyoshi, Nasushiobara (JP); Yukari Sone, Nasushiobara (JP)

(73) Assignee: CANON MEDICAL SYSTEMS CORPORATION, Otawara-Shi (JP)

( * ) Notice: Subject to any disclaimer, the term of this patent is extended or adjusted under 35 U.S.C. 154(b) by 103 days.

(21) Appl. No.: 15/946,133

(22) Filed: Apr. 5, 2018

(65) Prior Publication Data
US 2018/0303447 A1 Oct. 25, 2018

(30) Foreign Application Priority Data
Apr. 20, 2017 (JP) ................. 2017-083487

(51) Int. Cl.
| G06K 9/00 | (2006.01) |
| A61B 6/00 | (2006.01) |
| G06T 7/00 | (2017.01) |
| A61B 6/03 | (2006.01) |

(52) U.S. Cl.
CPC .............. *A61B 6/466* (2013.01); *A61B 6/44* (2013.01); *A61B 6/463* (2013.01); *A61B 6/505* (2013.01); *A61B 6/5217* (2013.01); *G06T 7/0012* (2013.01); *A61B 6/032* (2013.01); *G06T 2207/10081* (2013.01)

(58) Field of Classification Search
CPC ............................................ G06T 2207/30008
See application file for complete search history.

(56) References Cited

U.S. PATENT DOCUMENTS

| 2011/0306868 A1 | 12/2011 | Nagao |
| 2017/0256090 A1* | 9/2017 | Zhou ........................ G06T 15/08 |
| 2017/0262978 A1* | 9/2017 | Reynolds ............... A61B 5/055 |
| 2019/0066538 A1* | 2/2019 | Chao ..................... A61H 31/005 |

FOREIGN PATENT DOCUMENTS

| JP | 2010-063514 | 3/2010 |
| JP | WO 2010/098444 | 9/2010 |

OTHER PUBLICATIONS

Oikonomou et al (NPL "CT Imaging of Blunt Chest Trauma", Insights Imaging (2011) 2:281-295, p. 15). (Year: 2011).*

* cited by examiner

*Primary Examiner* — Oneal R Mistry
(74) *Attorney, Agent, or Firm* — Oblon, McClelland, Maier & Neustadt, L.L.P.

(57) ABSTRACT

The medical image diagnostic apparatus according to an embodiment includes processing circuitry. The processing circuitry is configured to: generate medical volume data including bones and an organ; identify, based on the volume data, the organ and an abnormal bone having an abnormal region of the bones; calculate, based on the organ and the abnormal bone of the volume data, an influence rate on the organ by the abnormal bone; and superimpose data indicating the influence rate on the image based on the volume data, thereby displaying the superimposed image on a display.

15 Claims, 12 Drawing Sheets

RENDERING IMAGE

MPR IMAGE

MEDICAL IMAGE DIAGNOSTIC APPARATUS, MEDICAL IMAGE PROCESSING APPARATUS AND NON-TRANSITORY COMPUTER READABLE MEDIUM ON WHICH MEDICAL IMAGE PROCESSING PROGRAM HAS BEEN STORED

CROSS-REFERENCE TO RELATED APPLICATION

This application is based upon and claims the benefit of priority from Japanese Patent Application No. 2017-083487, filed on Apr. 20, 2017, the entire contents of each of which are incorporated herein by reference.

FIELD

An embodiment as an aspect of the present invention relates to a medical image diagnostic apparatus, a medical image processing apparatus and a non-transitory computer readable medium on which a medical image processing program has been stored.

BACKGROUND

If ribs break deeply and stick to the internal organs, it may result in fatalities, so medical image processing apparatuses may observe the ribs of a patient. In that case, the medical image processing apparatus performs a 3D display of the ribs based on the volume data including the ribs, and a curved multi-planer reconstruction (CPR) display of them. The CPR display is expanded and displayed along the core line of the ribs. According to the CPR display, the entire ribs can be observed with a single image. With these displays, an operator such as a radiogram interpreter or the like is able to conveniently observe abnormal regions such as fractures and cracks in the ribs.

According to the CPR display, while it is easy to observe the abnormal region, there is a problem that it is difficult to confirm the influence on the organs around the ribs. This is because only ribs are displayed.

BRIEF DESCRIPTION OF THE DRAWINGS

In accompanying drawings.

DETAILED DESCRIPTION

A medical image diagnostic apparatus, a medical image processing apparatus and a non-transitory computer readable medium on which a medical image processing program has been stored according to embodiments will be described in detail with reference to the drawings.

The medical image diagnostic apparatus according to an embodiment includes processing circuitry. The processing circuitry is configured to: generate medical volume data including bones and an organ; identify, based on the volume data, the organ and an abnormal bone having an abnormal region of the bones; calculate, based on the organ and the abnormal bone of the volume data, an influence rate on the organ by the abnormal bone; and superimpose data indicating the influence rate on the image based on the volume data, thereby displaying the superimposed image on a display.

1. Medical Image Diagnostic Apparatus According to Embodiment

The medical image diagnostic apparatus according to the embodiment is a device capable of generating medical images including bones and an organ. For example, the medical image diagnostic apparatus is an X-ray computed tomography (CT) apparatus, a magnetic resonance imaging (MRI) apparatus, an ultrasonic diagnostic apparatus, or the like. Hereinafter, the case where the medical image diagnostic apparatus is the X-ray CT apparatus will be described.

It should be noted that data acquiring system based on an X-ray CT apparatus includes variations such as an R-R (Rotate/Rotate) system in which an X-ray tube and an X-ray detector rotate integrally around an object, and an S-R (Stationary/Rotate) system in which a large number of detection elements are arrayed in a ring form and only the X-ray tube rotates around the object. The present invention is applicable to either of the systems. Hereinafter, the X-ray CT apparatus according to the present embodiment will be explained on an exemplary case in which a third generation R-R system which is currently in dominant use is adopted.

Figure 1:
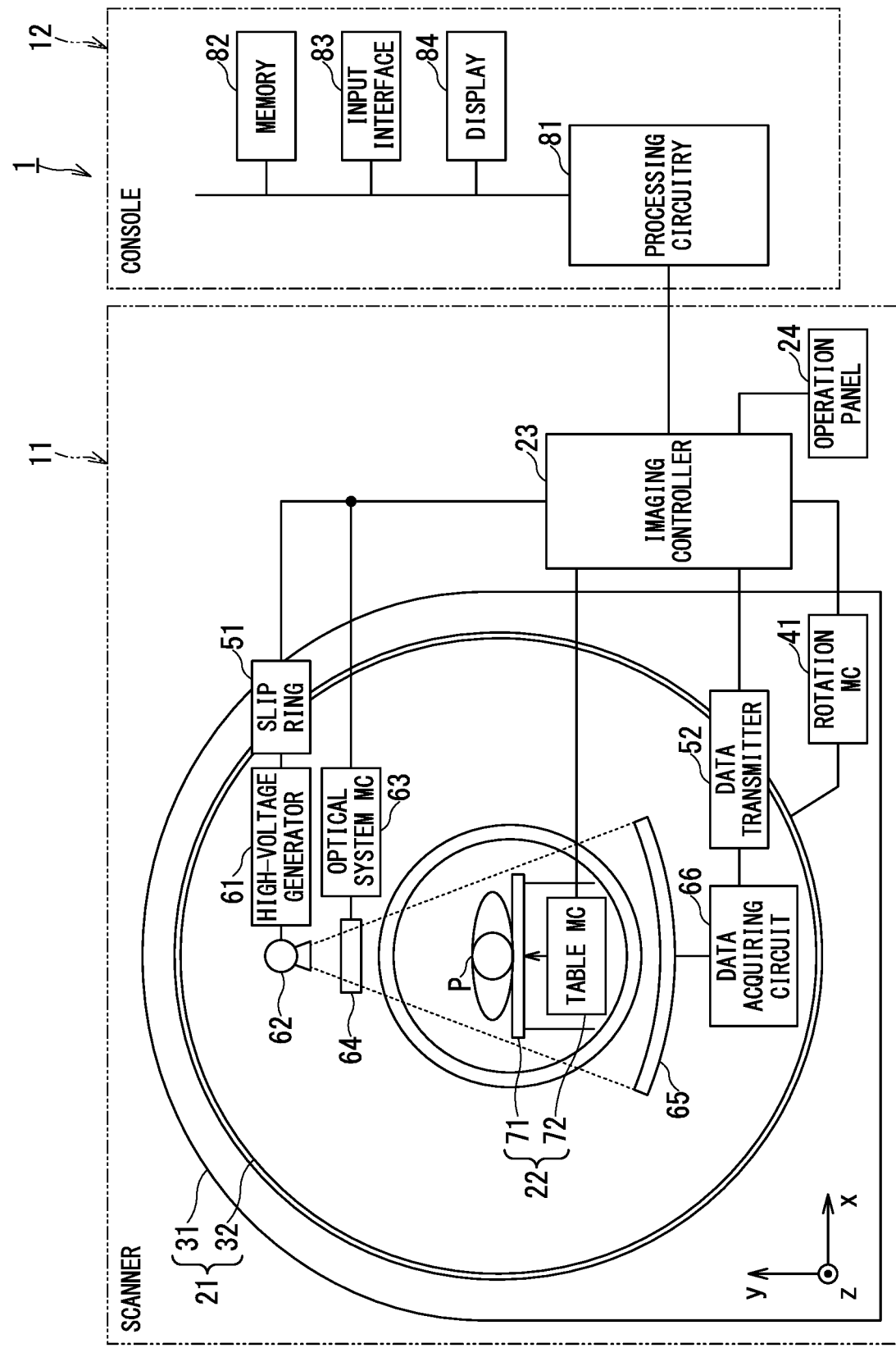
FIG. 1 is a schematic diagram showing a configuration example of an X-ray CT apparatus according to an embodiment.

FIG. 1 is a schematic diagram showing a configuration example of the X-ray CT apparatus according to the embodiment.

FIG. 1 shows an X-ray CT apparatus 1 according to the embodiment. The X-ray CT apparatus 1 includes a scanner 11 and a console 12. The console 12 is also referred to as an image processing apparatus. The scanner 11 of the X-ray CT apparatus 1 is typically installed in an examination room, and generates transmission data of X-rays relating to an object, for example, a patient P. On the other hand, the console 12, which is typically installed in a control room adjacent to the examination room, generates projection data based on the transmission data, and generates and displays an image such as a scanogram image or a tomographic image (reconstructed image).

The scanner 11 of the X-ray CT apparatus 1 includes a gantry 21, a bed 22, an imaging controller 23, and an operation panel 24.

The gantry 21 of the scanner 11 includes a fixed stand 31 fixed to a foundation part (not shown) and a rotator 32. The fixed stand 31 includes a rotation motor circuit 41.

The rotation motor circuit 41 is a motor circuit which supplies electric power to each motor unit (motor etc.) for moving the rotator 32 under the control of the imaging controller 23 to operate the each motor unit, and which rotates the rotator 32 with respect to the fixed mount 31 so that the rotator 32 rotate around an opening portion including a rotation center.

The fixed stand 31 and the rotator 32 include a slip ring 51 and a data transmitter 52.

The slip ring 51 is a connector for rotating contact which allows pass of electric current while a brush such as a carbon brush and a wire brush on the side of the fixed stand 31 is pressed from sideward against a ring-shaped electric circuit (metal ring), which is disposed in a concentric manner with the rotator 32, so as to be allowed to slip to each other.

The data transmitter 52 includes a transmission circuit on the side of the rotator 32 and a reception circuit on the side of the fixed stand 31. The transmission circuit transmits raw data generated by a data acquiring circuit 66 to be described below to the reception circuit in a non-contact manner. The reception circuit provides the raw data transmitted from the transmission circuit to the imaging controller 23 to be described later.

The rotator 32 includes a high-voltage generator 61, an X-ray source (for example, X-ray tube) 62, an optical system motor circuit 63, an X-ray optical system 64, an X-ray detector 65, and a data acquiring circuit 66. The rotator 32 is also called a rotatable frame. The rotator 32 holds components 61 to 66 integrally. That is, the rotator 32 can rotate integrally around the patient P with the X-ray tube 62 and the X-ray detector 65 being faced to each other. It is noted that a direction parallel with the central axis of rotation of the rotator 32, that is a longitudinal direction of a table 71, is defined as a z direction, and the plane orthogonal to the z direction is defined as an X direction and a y direction.

The high-voltage generator 61 provides power needed for executing various imaging to the X-ray tube 62 according to a control signal by the imaging controller 23 via the slip ring 51.

The X-ray tube 62 generates X-rays by causing an electron beam to collide with a target made of metal according to the tube voltage provided from the high-voltage generator 61, and radiates the X-rays toward the X-ray detector 65. A fan beam X-ray, a cone beam X-ray, and the like are formed by the X-rays radiated from the X-ray tube 62. The X-ray tube 62 is provided with power needed for radiation of X-rays through the control by the imaging controller 23.

The optical system motor circuit 63 is a motor circuit which supplies electricity to each motor unit (motor or the like) for moving the X-ray optical system 64 to operate each motor unit, thereby adjusting the irradiation range in the slice direction of X-rays in the X-ray optical motor circuit 64 through a control by the imaging controller 23.

The X-ray optical system 64 includes various instruments for controlling the radiation dose, irradiation range, shape, and radiation quality of X-ray beams. Specifically, the X-ray optical system 64 includes a wedge filter and a collimator. The wedge filter adjusts the X-ray dose of the X-rays generated at the X-ray tube 62. The collimator is a slit for reducing the irradiation range of X-rays for the X-rays of which radiation dose has been adjusted through the control by the optical system motor circuit 63.

The X-ray detector 65 is a detector of one-dimensional array type which has detection elements in the channel direction and a single detection element in the row (slice) direction. Alternatively, the X-ray detector 65 is a detector of matrix type, that is, of two-dimensional array type which has detection elements in the channel direction and detection elements in the slice direction. The X-ray detector 65 detects X-rays radiated from the X-ray tube 62.

The detector of two-dimensional array type is also called a multi-slice type detector. When the X-ray detector 65 is a multi-slice type detector, it is possible to perform an imaging of a 3-dimensional range having a width in the row direction by one rotation (or a half rotation+α) of the rotator 32, that is a volume imaging.

The data acquiring circuit 66 has DASs (Data Acquisition Systems). Each DAS performs data acquiring. Each DAS amplifies the signal of transmission data detected by each detection element of the X-ray detector 65, and transforms it into raw data which is a digital signal. Each DAS sends the raw data to the image controller 23 via the data transmitter 52.

The bed 22 of the scanner 11 includes a table 71 and a table motor circuit 72. The table 71 is able to place a patient P thereon.

The table motor circuit 72 is a motor circuit which supplies electricity to each motor unit (motor or the like) for moving the table 71 to operate each motor unit, thereby causing the table 71 to move up and down along the y direction, and to enter/retreat in the z direction through the control by the imaging controller 23. The table motor circuit 72 causes the patient P placed on the table 71 to be inserted toward the opening portion including the rotational center of the rotator 32, and causes the patient P placed on the table 71 to retreat from the opening portion.

The imaging controller 23 includes processing circuitry (not shown) and a memory (not shown), etc. In accordance with an instruction from the console 12, the imaging controller 23 controls the rotation motor circuit 41, the high-voltage generator 61, the X-ray tube 62, the X-ray detector 65, and the optical system motor circuit 63, etc. according to the imaging condition such as the tube current [mA], the tube voltage [kV], the X-ray intensity control condition (modulation condition), the rotation speed of the rotator 32, or the focal point size of the X-ray tube 62, thereby executing the chest imaging of the patient P. The imaging controller 23 may perform imaging (also referred to as "volume scan") to acquire volume data relating to one phase, or imaging (also referred to as "dynamic scan") for to acquire volume data relating to multiple time phases.

The operation panel 24, which is provided on both sides or in the front and rear of the opening portion of the gantry 21, accepts operations which the operator performs while confirming the status of the patient P. Specifically, the operation panel 24 accepts instructions of moving, stopping, and automatically feeding the table 71.

The console 12 is composed based on a computer. The console 12 is made up of basic hardware elements such as processing circuitry 81, a memory (or storage) 82, an input interface 83, and a display 84. The processing circuitry 81 is interconnected with each hardware component, which constitutes the console 12, via a bus as a common signal transmission line. It should be noted that the console 12 may include a storage medium drive.

The processing circuitry 81 means any one of dedicated or general central processing unit (CPU) and a micro-processor unit (MPU), an application specific integrated circuit (ASIC), and a programmable logic device. The programmable logic device may be, for example, any one of a simple programmable logic device (SPLD), a complex programmable logic device (CPLD), a field programmable gate array (FPGA) and the like. The processing circuitry 81 reads programs stored in the memory circuitry 82 or directly implemented in the processing circuitry 81 and executes these programs to achieve the following functions.

The processing circuitry 81 may be a single processing circuit or a combination of multiple processing circuit elements. In the latter case, the memory 82 includes multiple memory elements each storing an element of a program, each of the multiple memory elements is provided for each of the multiple processing circuit elements. Alternatively, the memory 82 includes a single memory storing the program, the single memory is provided for the multiple processing circuit elements.

The memory 82 is made up of semiconductor memory devices such as a RAM (Random Access Memory) and a flash memory, hard discs, optical discs, and the like. The memory 82 may be made up of a portable media such as a USB (Universal Serial Bus) memory and a DVD (Digital Video Disk). The memory 82 stores various processing programs (including application programs, as well as an OS (Operating System)) used in the processing circuitry 81, data necessary for executing the programs, and image data. Moreover, the OS may include a graphic user interface (GUI) which frequently uses graphics for displaying information for the operator on the display 84, and allows basic operations to be performed by use of the input interface 83.

The input interface 83 includes an input device which can be operated by the operator, and an input circuit for inputting a signal from the input device. The input device includes a pointing device (for example, a mouse), a keyboard, various buttons, and the like. When the input device is operated by the operator, the input circuit generates a signal corresponding to the operation and outputs it to the processing circuitry 81. It should be noted that the console 12 may include a touch panel in which the input device is integrated with the display 84.

The display 84 is a display device such as a liquid crystal display panel, a plasma display panel, and an organic EL (Electro Luminescence) panel. The display 84 displays a generated tomographic image and an image on which data indicating an influence rate is superimposed, according to control by the processing circuitry 81.

It should be noted that the console 12 may include a communication control circuit which is an interface (IF) configured by a connector conforming to a parallel connection specification or a serial connection specification. The communication control circuit transmits and receives, when the X-ray CT apparatus 1 is provided on the network such as a local area network (LAN), information to and from external devices on the network. For example, the communication control circuit transmits image data, generated by the X-ray CT apparatus 1, to an external device such as an image managing device or a diagnostic terminal (not shown), and performs a communication operation with the external device.

Subsequently, functions of the X-ray CT apparatus 1 will be described.

Figure 2:
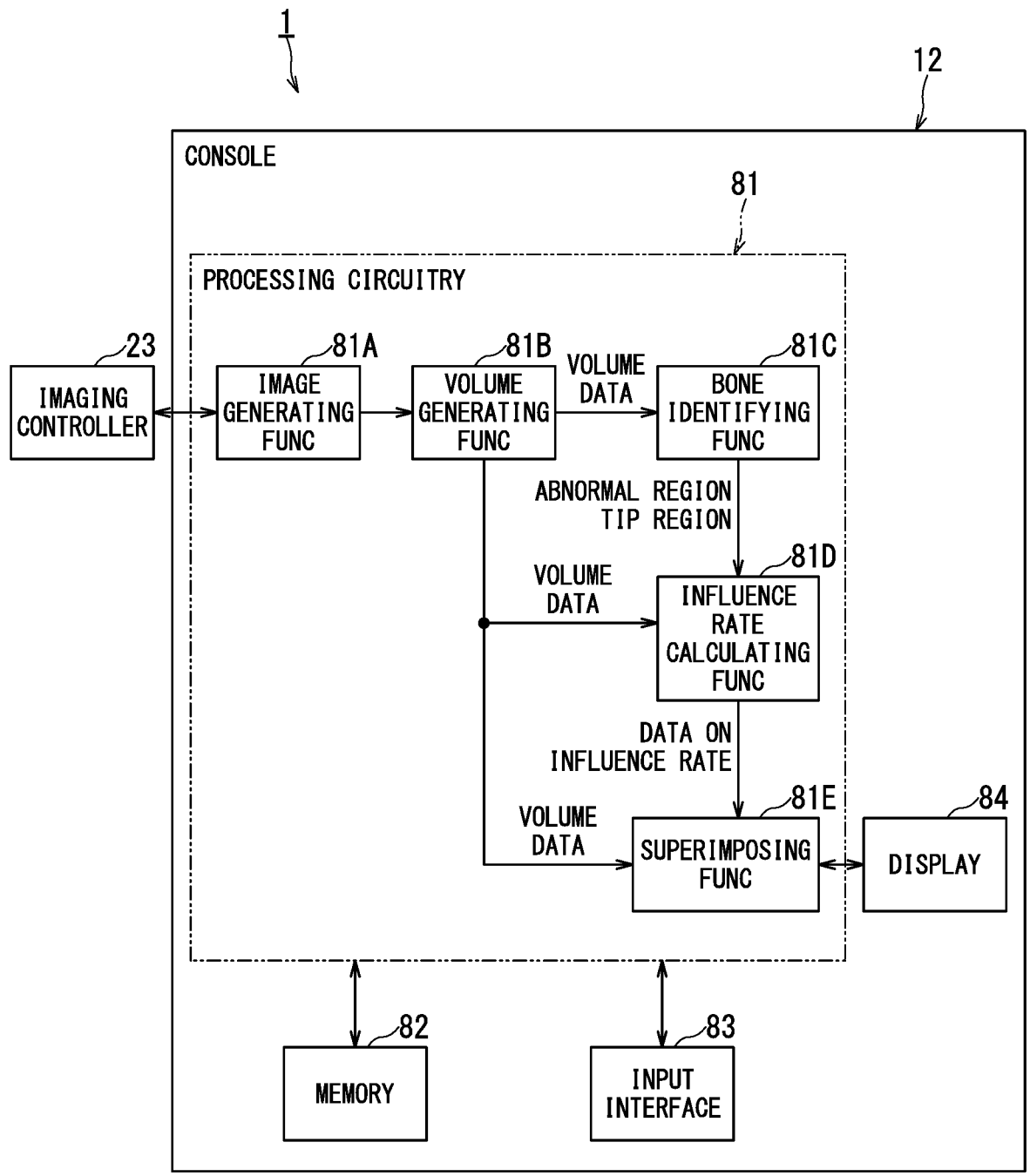
FIG. 2 is a block diagram showing functions of the X-ray CT apparatus according to the embodiment.

FIG. 2 is a block diagram showing functions of the X-ray CT apparatus.

When the processing circuitry 81 of the console 12 executes a program, the X-ray CT apparatus 1 achieves an image generating function (image generating unit) 81A, a volume generating function (volume generating unit) 81B, a bone identifying function (bone identifying unit) 81C, an influence rate calculating function (influence rate calculating unit) 81D, and a superimposing function (superimposing unit) 81E. All or part of the functions 81A to 81E may be installed as the hardware included in the console 12. All or part of the functions 81A to 81E may be included not only in the console 12 but also in the imaging controller 23.

The image generating function 81A includes a function of controlling, based on imaging conditions, the imaging controller 23 to execute chest imaging of the patient P, and a function of generating a tomographic image including bones and an organ, based on data transmitted from the imaging controller 23 by chest imaging. In the embodiment, the organ is also called vitals. An example of the organ contained in the tomographic image by chest imaging includes heart, stomach, lung, liver, blood vessel, nerve or the like.

As an image reconstruction method for generating the tomographic image, an analytical method typified by convolution correction back projection (CBP) method or filtered back projection (FBP) method, and algebraic method are known. The image generating function 81A utilizes these methods. The algebraic method is generally called an iterative reconstruction (IR) method because the tomographic image is obtained using an iterative method.

Further, the image generating function 81A may include a function of displaying the generated tomographic image on the display 84.

The volume generating function 81B includes a function of performing, based on the tomographic images generated by the image generating function 81A, interpolation processing as necessary, thereby generating medical volume data including the bones and the organ. The volume data is an aggregate of multiple voxel values.

The bone identifying function 81C includes a function of identifying, based on the volume data generated by the volume generating function 81B, a bone (hereinafter referred to as "abnormal bone") having an abnormal region of the bones. In the embodiment, the abnormal region means a part which is a crack or fracture of the abnormal bone. The abnormal bone includes the abnormal region and a part other than the abnormal region, for example, a tip (hereinafter referred to as "tip region") on the sternum side or spine side, a rod-like part close to the tip, and the like.

The tip region of the abnormal bone or the like adversely affects organs such as sticking to the internal or compressing the internal organs. Hereinafter, a case where the bone identifying function 81C identifies, based on the volume data, the abnormal region and the tip region of the abnormal bone will be described. Each of the abnormal region and the tip region of the abnormal bone is specified by the operator via the input interface 83. Alternatively, each of the abnormal region and the tip region of the abnormal bone is specified by automatically extracting, based on the volume data, using a method of continuity analysis of pixel value (CT value) or the like.

The influence rate calculating function 81D includes a function of calculating, based on the abnormal region and the tip region of the abnormal bone identified by the bone identifying function 81C from the volume data generated by the volume generating function 81B, an influence rate on the organ of the abnormal region or the tip region. For example, the influence rate calculating function 81D calculates a distance between the abnormal bone and the organ, and calculates the influence rate according to the distance.

The superimposing function 81E includes a function of superimposing data on the influence rate, calculated by the influence rate calculating function 81D, on the image based on the volume data generated by the volume generating function 81B, and displaying the superimposed data on the display 84.

The specific operation of the functions 81A to 81E will be described later with reference to FIGS. 3 to 10.

Figure 3:
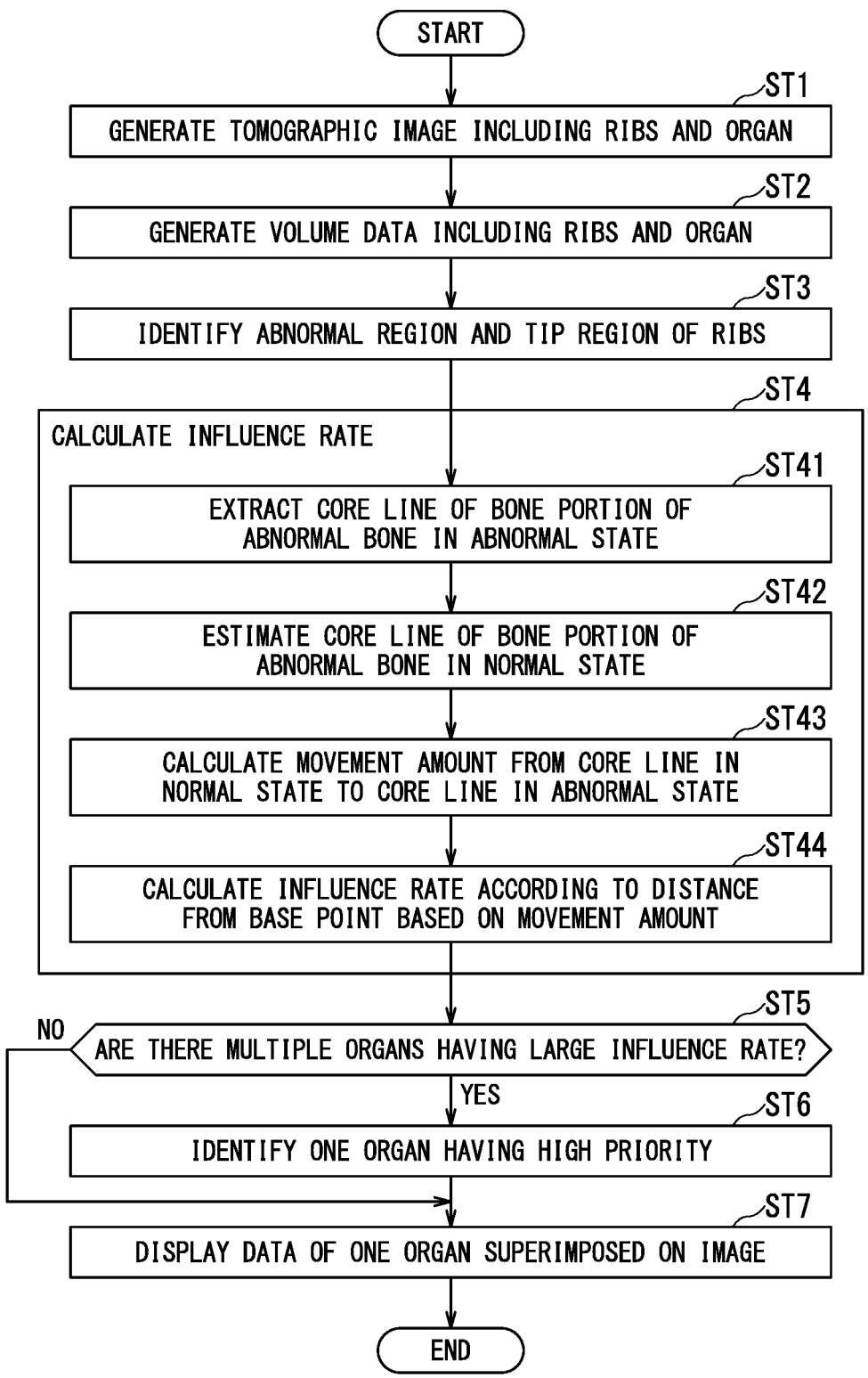
FIG. 3 is a flowchart showing an operation example of the X-ray CT apparatus according to the embodiment.

FIG. 3 is a flowchart showing an operation example of the X-ray CT apparatus 1.

The image generating function 81A controls, based on the imaging conditions, the imaging controller 23 to perform imaging of the chest of the patient P, and generates, based on data transmitted from the imaging controller 23 by chest imaging, a tomographic image including ribs and an organ (step ST1). The image generating function 81A may display the tomographic image, generated in step ST1, on the display 84.

The volume generating function 81B performs, based on the tomographic images generated in step ST1, interpolation processing as needed, thereby generating volume data including the ribs and the organ (step ST2). The bone identifying function 81C identifies, based on the volume data generated in step ST2, an abnormal bone of the ribs, for example, an abnormal region and a tip region of the abnormal bone (step ST3).

In the embodiment, in step ST3, the bone identifying function 81C may use the machine learning such as the deep learning to identify the characteristic structure from the volume data. For example, in the field of image recognition, a learning method using a convolutional neural network (CNN) which is one of the deep learning is known. The bone identifying function 81C performs the machine learning using the machine learning volume data accumulated in the memory 82, thereby generating artificial intelligence (AI) for identifying the characteristic structure. Then, using the AI, the bone identifying function 81C identifies the characteristic structure, for example, the abnormal bone or the abnormal region and tip region of the abnormal bone, or the like from the volume data generated in step ST2. Further, the identified result is accumulated in the memory 82.

The influence rate calculating function 81D calculates, based on the abnormal region and the tip region of the abnormal bone identified in step ST3 from the volume data generated in step ST2, an influence rate on the organ of the abnormal region or the tip region (step ST4). In step ST4, the influence rate calculating function 81D calculates a distance between a bone portion of the abnormal bone and the organ, the bone portion being between the abnormal region and the tip region of the abnormal bone, and calculates the influence rate according to the distance.

First, in step ST4, the influence rate calculating function 81D extracts, based on the abnormal region and the tip region identified in step ST3, the bone portion between the abnormal region and the tip region in an abnormal state, for example, a core line of the bone portion in the abnormal state (step ST41). Hereinafter, the case where the bone portion to be extracted is the core line of the bone portion will be described, but it is not limited to that case. For example, the bone portion to be extracted may be an outline of the bone portion or the like.

Figure 4:
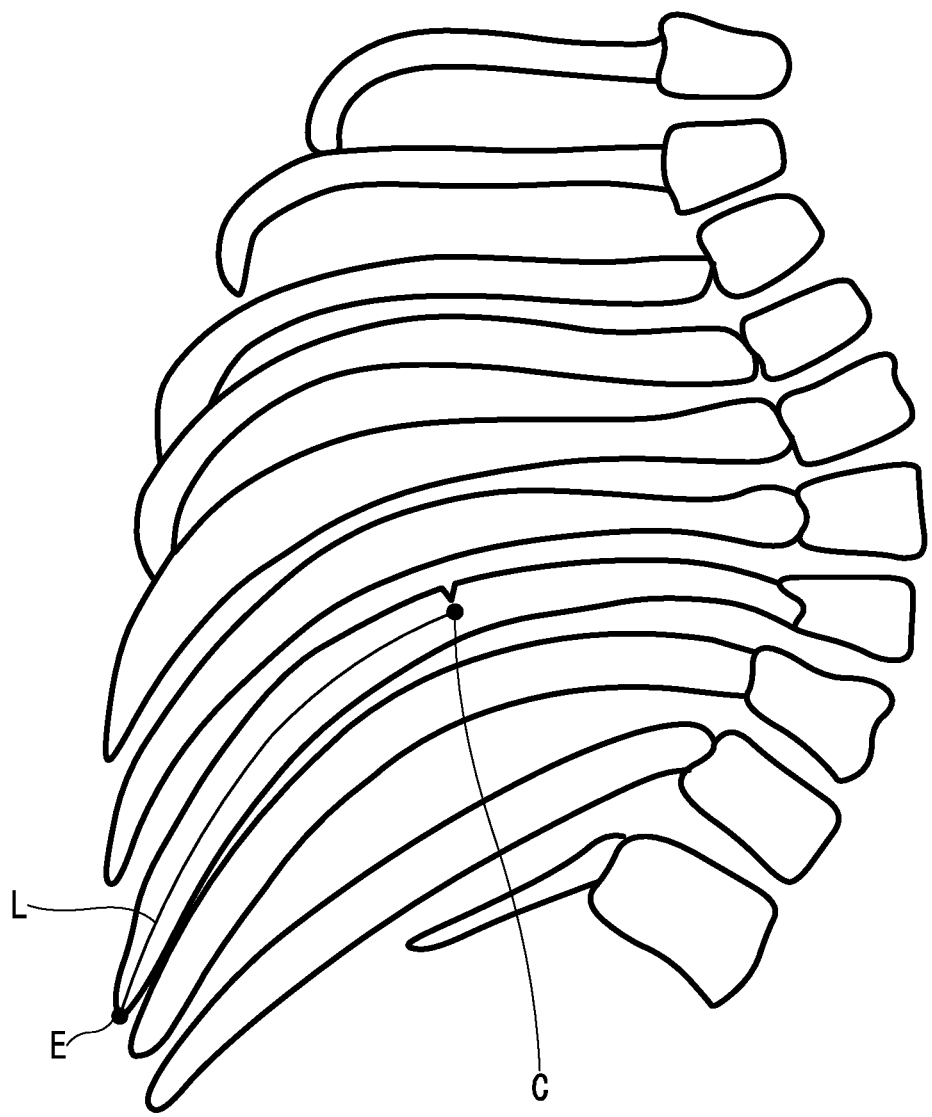
FIG. 4 is a diagram for explaining a method of extracting a core line between an abnormal region and a tip region.

FIG. 4 is a diagram for explaining a method of extracting a core line between the abnormal region and the tip region.

FIG. 4 is a view of volume data including the ribs of the patient P as seen from the left side of the patient P. A crack C as an abnormal region and a tip region E on a breastbone side of a bone having a crack C are shown on the volume data. It should be noted that the crack C can be regarded as a position where the identified crack position is shifted onto the core line, and the tip region E can be regarded as a position where the identified tip position is shifted onto the core line. The bone portion between the abnormal region and the tip region is extracted as the core line L between the crack C and the tip region E.

Returning to the explanation of FIG. 3, in step ST4, the influence rate calculating function 81D extracts, based on the volume data generated in step ST2, a core line of a bone (hereinafter referred to as "normal bone") other than the abnormal bone, and estimates, based on the core line of the normal bone, a core line of the abnormal bone in a normal state. For example, in step ST4, the influence rate calculating function 81D extracts, based on the volume data, core lines of normal bones above and below the abnormal bone of the ribs, and estimates, based on the core lines of the normal bones, a core line of the abnormal bone in the normal state (step ST42). That is, in step ST42, the influence rate calculating function 81D estimates a core line of the abnormal bone, which is normal before the abnormality occurs, based on the surrounding normal bones.

Figure 5:
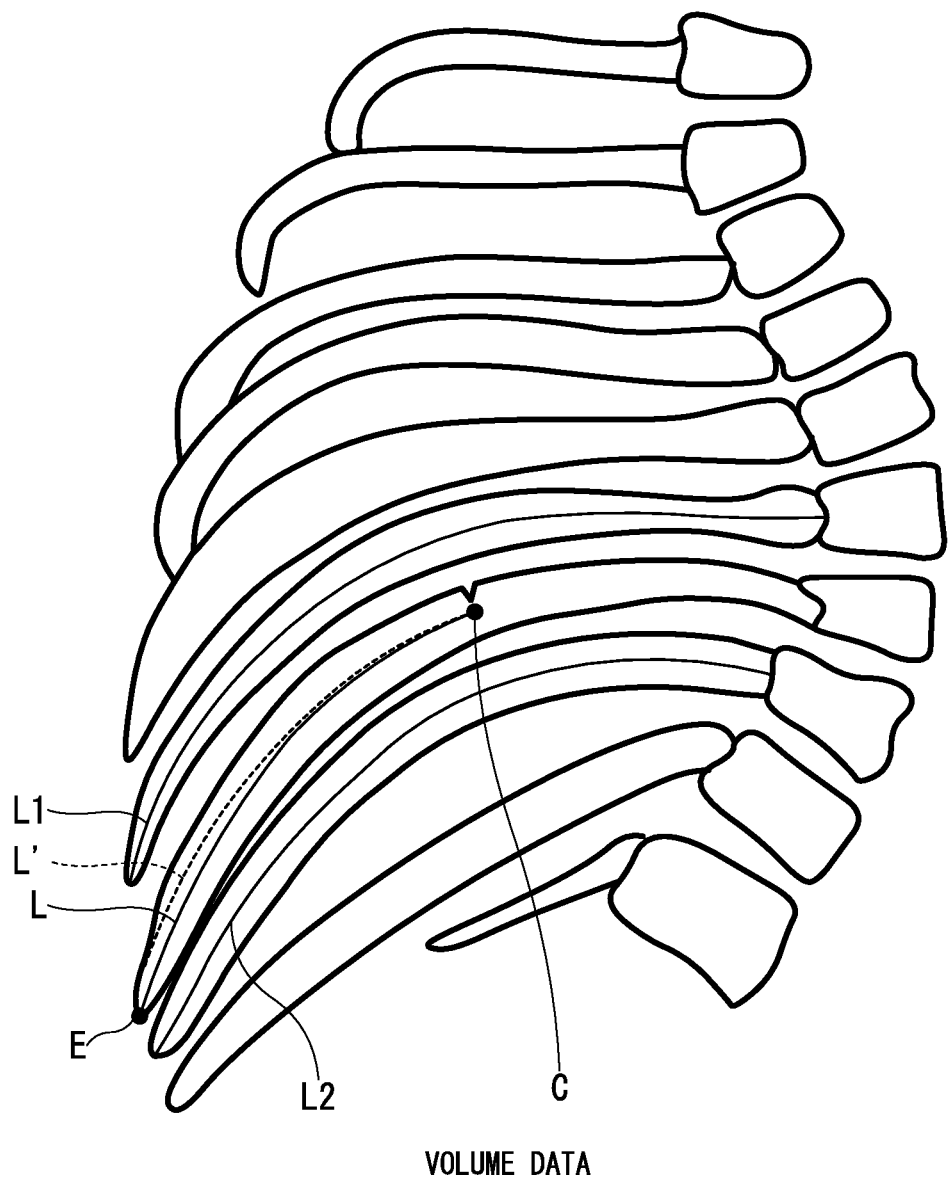
FIG. 5 is a diagram for explaining a method of estimating a core line of an abnormal bone.

FIG. 5 is a diagram for explaining a method of estimating the core line of the abnormal bone.

FIG. 5 is a view of the volume data including the ribs of the patient P as seen from the left side of the patient P. On the volume data, the crack C, the tip E, and the core line L are illustrated, as shown in FIG. 4. On the volume data, the core lines L1 and L2 of the bones related to the upper and lower sides of the bone having the crack C are extracted. The core line L' in the normal state of the bone portion having the crack C is estimated as a substantially intermediate line between the core lines L1 and L2.

Returning to the explanation of FIG. 3, in step ST4, the influence rate calculating function 81D calculates a movement amount from the core line of the abnormal bone in the normal state estimated in step ST42, to the core line of the abnormal bone in the abnormal state extracted in step ST41 (step ST43).

Figure 6:
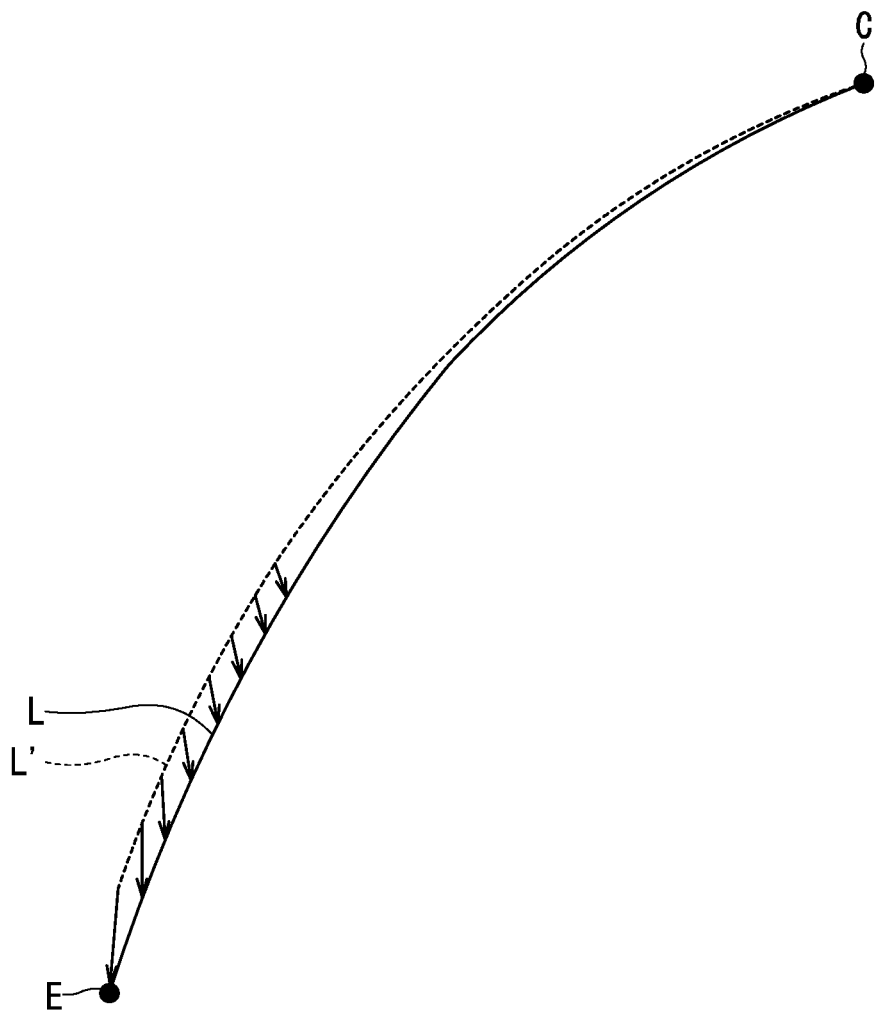
FIG. 6 is a diagram for explaining a method of calculating a movement amount of the core line of the abnormal bone.

FIG. 6 is a diagram for explaining a method of calculating the movement amount of the core line of the abnormal bone.

FIG. 6 shows an enlarged view of the cracks C, the tip region E, and the core lines L and L' shown in FIG. 5. As shown in FIG. 6, vectors from the points of the estimated normal core line L' to the abnormal core line L are calculated. Based on a direction of each vector, a movement direction of the core line of the bone portion having the crack C is defined. Based on a length of each vector, a movement amount of the core line of the bone portion having the crack C is defined.

In the embodiment, a start point and an end point of each vector are obtained so that a length from the crack C is the same. Specifically, first, the length Q [mm] of the core line L' and the length R [mm] of the core line L are obtained. Then, a vector is obtained so that a point on the core line L' where the length from the crack C is q [mm] is set as the start point, and that a point on the core line L where the length from the crack C is q×R/Q is set as the end point. Vectors are obtained for the lengths q [mm], respectively. It should be noted that q [mm] may not be the length from the crack C but may be a length from each tip region.

Returning to the explanation of FIG. 3, in step ST4, the influence rate calculating function 81D sets a base point, based on the movement amount calculated in step ST43, and calculates an influence rate on the organ by the abnormal region or the tip region of the abnormal bone according to a distance from the base point (step ST44).

Figure 7:
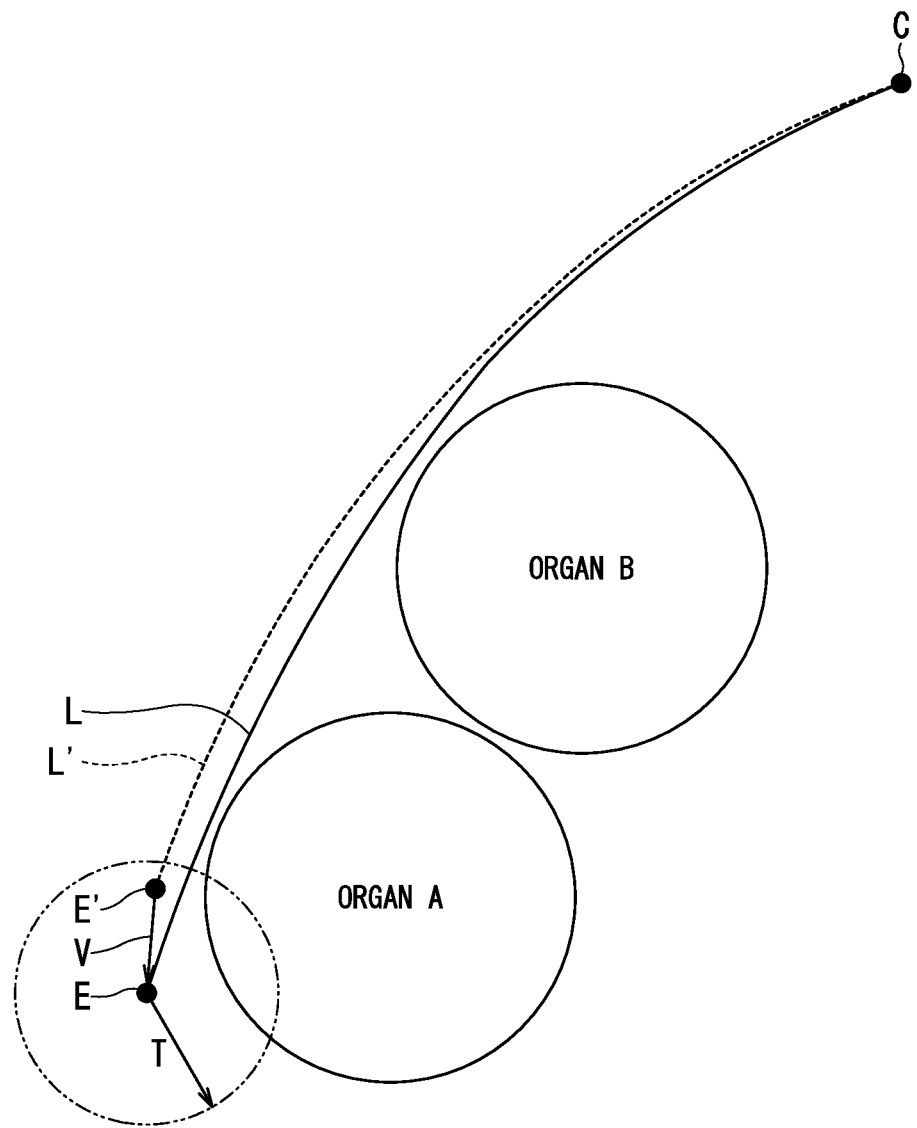
FIG. 7 is a diagram for explaining a method of calculating an influence rate.

FIG. 7 is a diagram for explaining a method of calculating the influence rate.

FIG. 7 is a view showing the crack C, the tip region E, and the core lines L and L' shown in FIG. 6. In FIG. 7, a vector having a maximum length (a vector V of the start point E' in FIG. 7) is selected from the vectors calculated in FIG. 6. One or multiple threshold values (one threshold value T in FIG. 7) indicating a distance from the end point E of the vector V are defined. By setting multiple threshold values, it is also possible to gradually classify the influence rate by the crack C or the tip region E. The end point E of the vector V having the maximum length is set as the base point. The organ A including the region within the threshold T from the end point E among the organs A and B is identified as having a high influence rate.

It should be noted that the crack C and the tip region E are expected to have large bone movements due to breathing and the like. Therefore, in addition to the distance (for example, the threshold value T), the influence rate calculating function 81D calculates an influence rate on the organ by the abnormal region or the tip region of the abnormal bone according to a distance from the crack C or the tip region E to the base point (for example, the end point E of the vector having a maximum length). For example, the influence rate calculating function 81D performs weighting so that the influence rate increases as the start point of the selected vector is closer to the crack C or the tip region E. The influence rate calculating function 81D may calculate an influence rate on the organ by the crack C or the tip region of the abnormal bone according to the type of organ. For example, when the organ is a lung with high importance, the influence rate calculating function 81D performs weighting so as to increase the influence rate.

In the embodiment, in step ST4, the influence rate calculating function 81D may use the above mentioned machine learning such as the deep learning to calculate the core line, the movement amount and the influence rate. For example, the influence rate calculating function 81D performs the machine learning using the machine learning volume data accumulated in the memory 82, thereby generating the AI for calculating the influence rate. Then, using the AI, the influence rate calculating function 81D calculates the influence rate from the volume data generated in step ST2. Alternatively, the influence rate calculating function 81D performs the machine learning using the machine learning parameter data such as the core line accumulated in the memory 82, thereby generating the AI for calculating the influence rate. Then, using the AI, the influence rate calculating function 81D calculates the influence rate from the core line extracted in step ST41. Further, the calculated result is accumulated in the memory 82.

Returning to the explanation of FIG. 3, the superimposing function 81E determines whether or not there are multiple organs having a large influence rate in step ST4 (step ST5). If it is determined as "YES" in step ST5, that is, if it is determined that there are multiple organs having the large influence rate, the superimposing function 81E identifies one organ having a high priority based on priorities assigned in advance to the multiple organs (step ST6).

The superimposing function 81E superimposes data of one organ identified in step ST6 on an image based on the volume data generated in step ST2, and displays the superimposed image on the display 84 (step ST7). It should be noted that if it is determined as "YES" in step ST5, that is, if it is determined that there are multiple organs which are considered to have the large influence rate, the superimposing function 81E may superimpose data of all the organs on the image, and display the superimposed image on the display 84 (step ST7).

On the other hand, If it is determined as "NO" in step ST5, that is, if it is determined that there is one organ having the large influence rate, the superimposing function 81E superimposes data of the one organ calculated in step ST4 on the image based on the volume data generated in step ST2, and displays the superimposed image on the display 84 (step ST7). It should be noted that the image based on the volume data is a rendering image such as a volume rendering image or a surface rendering image, a multi-planar reconstruction (MPR) image, a CPR image, or the like.

Figure 8:
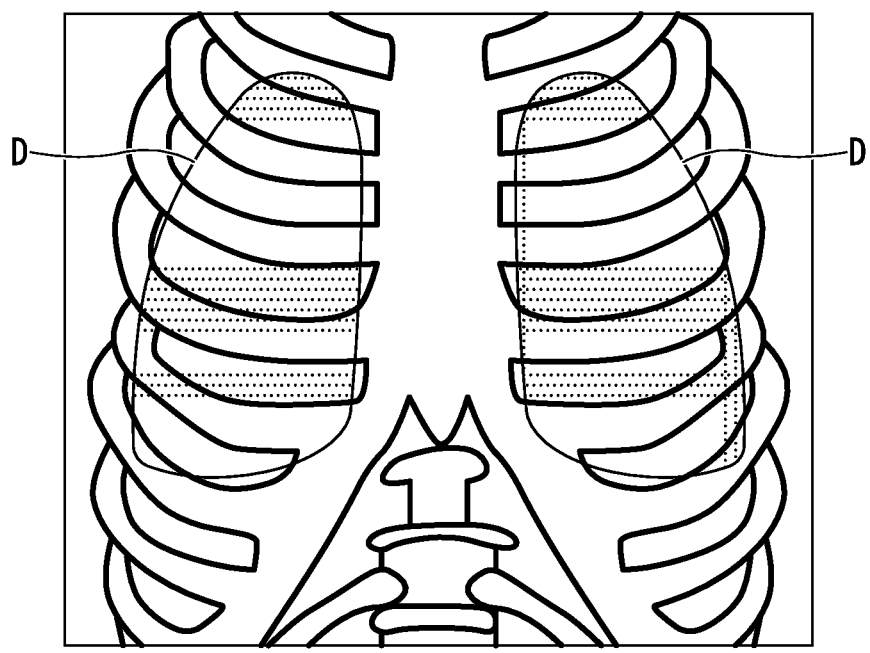
FIG. 8 is a diagram showing an example of an image on which data of the influence rate on lungs is superimposed.
Figure 9:
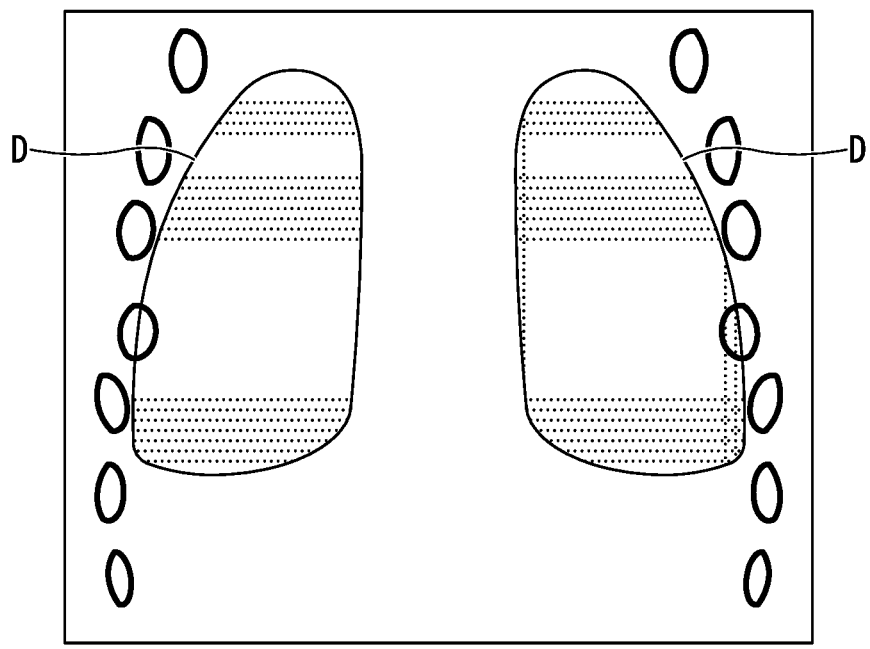
FIG. 9 is a diagram showing an example of an image on which data of the influence rate on lungs is superimposed.

Each of FIGS. 8 and 9 is a diagram showing an example of the image on which the data of the influence rate on lungs is superimposed.

FIG. 8 shows a rendered image, based on volume data, in which data D indicating that the influence rate to the lungs by the abnormal region or the tip region is large is superimposed. FIG. 9 shows an MPR image of an arbitrary cross-section, based on the volume data, in which data D indicating that the influence data to the lungs by the abnormal region or the tip region is large is superimposed. By displaying these images, it is possible for the operator to visually recognize that the influence rate by the abnormal region or the tip region is large with respect to the lungs of the patient P.

Further, the cross-section (MPR cross-section) related to the MPR image may be set based on the direction of the vector shown in FIG. 7. Each of FIGS. 10A and 10B is a diagram showing the MPR cross-section set from the direction of the vector shown in FIG. 7.

Figure 10A:
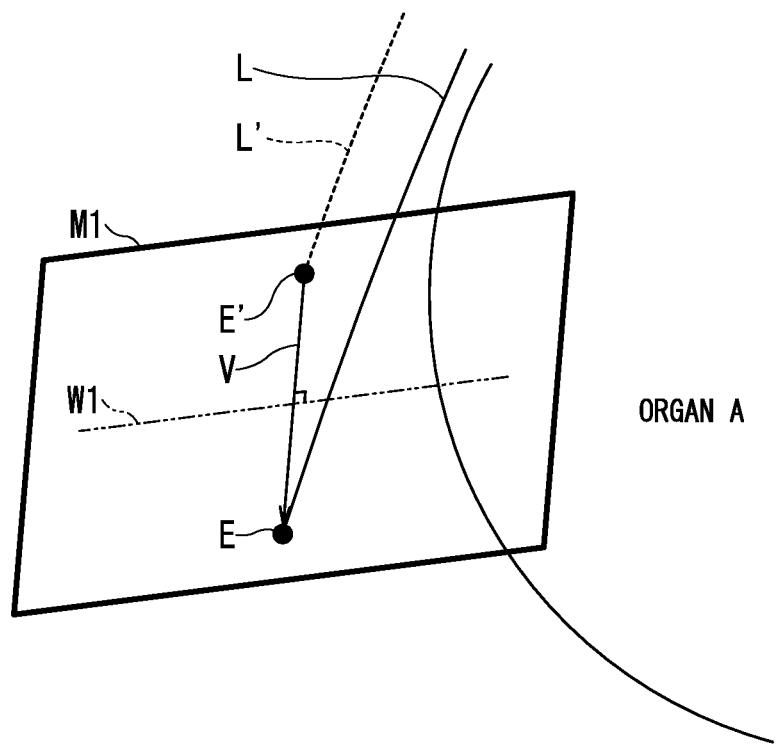
FIG. 10A is a diagram showing an MPR cross-section set from a direction of the vector shown in FIG. 7.
Figure 10B:
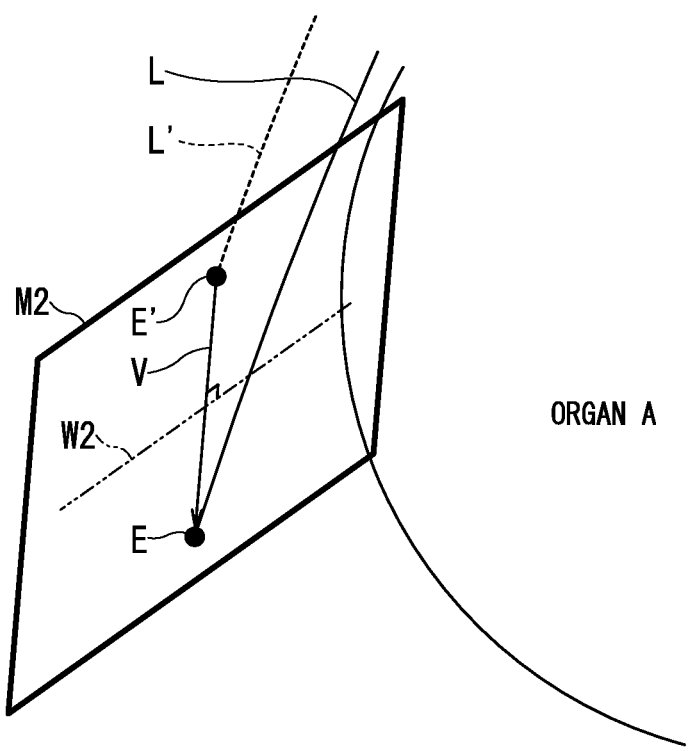
FIG. 10B is a diagram showing an MPR cross-section set from a direction of the vector shown in FIG. 7.

FIG. 10A shows the vector V of the start point E' and the end point E shown in FIG. 7, and its orthogonal line W1. The MPR cross-section M1 is defined as a cross-section including the vector V and the orthogonal line W1. By displaying the image relating to the MPR cross-section M1 determined in this way, it is possible for the operator to visually recognize the influence rate on the organ A by the abnormal region or the tip region. It should be noted that the cross-section set from the direction of the vector V shown in FIG. 7 is not limited to the case of the MPR cross-section M1 shown in FIG. 10A. For example, the cross-section may be the case of the MPR cross-section M2 including the vector V and its orthogonal line W2, as shown in FIG. 10B. This is because multiple orthogonal lines of the vector V can be obtained.

First Modified Example

In a first modified example, a case where the influence rate calculating function 81D uses multiple volume data relating to time phases by dynamic scanning will be described. Using the multiple volume data, the influence rate calculating function 81D calculates the influence rate on the organ by the abnormal region or the tip region by using any one of the following two methods.

First, the influence rate calculating function 81D obtains the movement amount of the bone portion for each of the multiple volume data, and calculates the influence rate on the organ by the abnormal region or the tip region, using volume data having a maximum movement amount. In this case, the influence rate calculating function 81D obtains the vector shown in FIG. 7 for each of the multiple volume data, and uses the volume data including the vector having the maximum length.

Second, the influence rate calculating function 81D calculates the influence rate on the organ by the abnormal region or the tip region, using volume data concerning a preset time phase, that is, a timing at which the lungs have most expanded or a timing at which the lungs have most contracted. This is because the influence rate on the lung by the abnormal region or the tip region greatly fluctuates according to the expansion and contraction movements of the lungs.

As described above, the influence rate calculating function 81D may calculate, in addition to the distance (for example, the threshold value T shown in FIG. 7), the influence rate on the organ by the crack C or the tip region E according to the distance between the base point (for example, the end point E of the vector having the maximum length shown in FIG. 7) and the crack C or the tip region E. However, instead of the distance between the base point and the crack C or the tip region E, the amount of change of the length of the vector related to the base point over time may be used.

In this case, the influence rate calculating function 81D acquires the vector shown in FIG. 7 for each of the multiple volume data, and acquires t the amount of change of the length of the vector related to the base point for each position of the bone portion over time. Then, in addition to the distance (for example, the threshold value T shown in FIG. 7) calculated using one of the volume data of the multiple volume data, the influence rate calculating function 81D calculates the influence rate on the organ by the abnormal region or the tip region, in accordance with the amount of change of the length of the vector. For example, the influence rate calculating function 81D weights the influence rate as the amount of change of the length of the vector related to the base point increases.

Second Modified Example

In the second modified example, the influence rate calculating function 81D may calculate the influence rate on the organ by the abnormal region or the tip region of the abnormal bone, by using multiple volume data generated in different examinations (for example, different dates and times) in the same patient and in the same site, The degree of influence on organs by the part may be calculated. As to the specific calculation method of the influence rate in the second modified example, the method described in the first modified example can be applied.

Third Modified Example

In the third modified example, the influence rate calculating function 81D may estimate an impact rate (Newton) on the organ by the abnormal bone, based on a bone density estimated based on the volume data (for example, the CT value) and the movement amount of the abnormal bone (for example, the length of the vector V shown in FIG. 7). In this case, the superimposing function 81E may superimpose the impact degree of the organ, on the image generated by superimposing the data of the influence rate on the image based on the volume data, and display the superimposed image on the display 84. The impact rate on the organ is expressed, for example, by a color or a character string corresponding to the degree of impact. Thereby, it is possible to present the impact rate on the organ by the abnormal bone to the operator.

As described above, according to the X-ray CT apparatus 1, it is possible to present to the operator the influence rate on the organ by the crack C or the tip portion E of the abnormal bone.

2. Medical Image Processing Apparatus According to Embodiment

Figure 11:
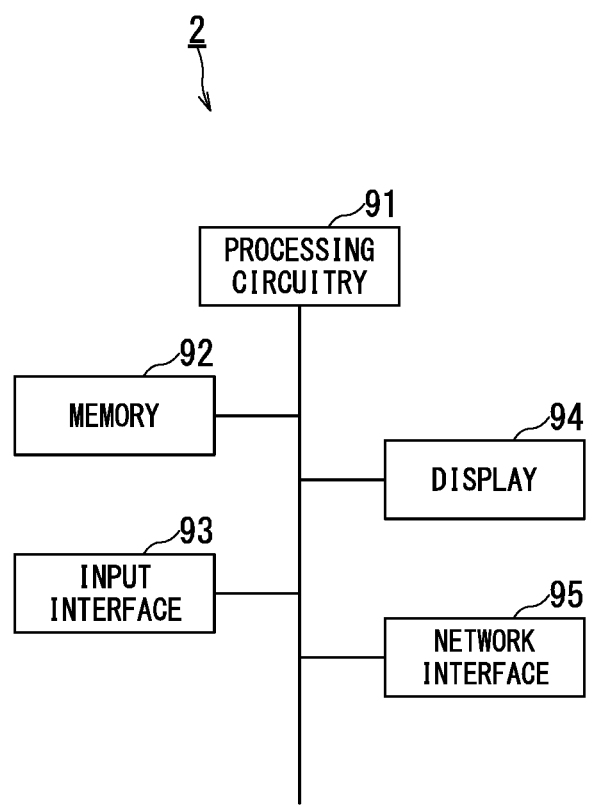
FIG. 11 is a schematic diagram showing a configuration example of a medical image processing apparatus according to an embodiment.

FIG. 11 is a schematic diagram showing a configuration example of the medical image processing apparatus according to the embodiment.

FIG. 11 shows a medical image processing apparatus 2 according to the embodiment. The medical image processing apparatus 2 is a medical image management apparatus (image server), a workstation, an image interpretation terminal or the like, and is provided on a medical image system connected via a network. It should be noted that the medical image processing apparatus 2 may be an offline apparatus.

The medical image processing apparatus 2 includes processing circuitry 91, a memory 92, an input interface 93, a display 94, and a network interface 95.

The processing circuitry 91 has the same configuration as the processing circuitry 81 shown in FIG. 1. The processing circuitry 91 comprehensively controls processing operations of each of the units 92 to 95 by reading out and executing a program stored in the memory 92 or directly incorporated in the processing circuitry 91.

The memory 92 has the same configuration as the memory 82 shown in FIG. 1. The memory 92 stores various processing programs used in the processing circuitry 91, and data necessary for executing the programs. In addition, the OS may include the GUI which frequently uses graphics for displaying information for the operator on the display 94, and allows basic operations to be performed by use of the input interface 93.

The input interface 93 has the same configuration as the input interface 83 shown in FIG. 1. When the input device is operated by the operator, the input circuit generates a signal corresponding to the operation and outputs it to the processing circuitry 91. It should be noted that the medical image processing apparatus 2 may include a touch panel in which the input device is integrated with the display 94.

The display 94 has the same configuration as the display 84 shown in FIG. 1. The display 94 displays the tomographic image and the superimposed image generated under the control of the processing circuitry 91.

The network interface 95 is constituted by connectors conforming to the parallel connection specification and the serial connection specification. The network interface 95 has a function of performing communication control according to each standard and connecting to the network through a telephone line. Thereby, it is possible to connect the medical image processing apparatus 2 to the network.

Subsequently, functions of the medical image processing apparatus 2 will be described.

Figure 12:
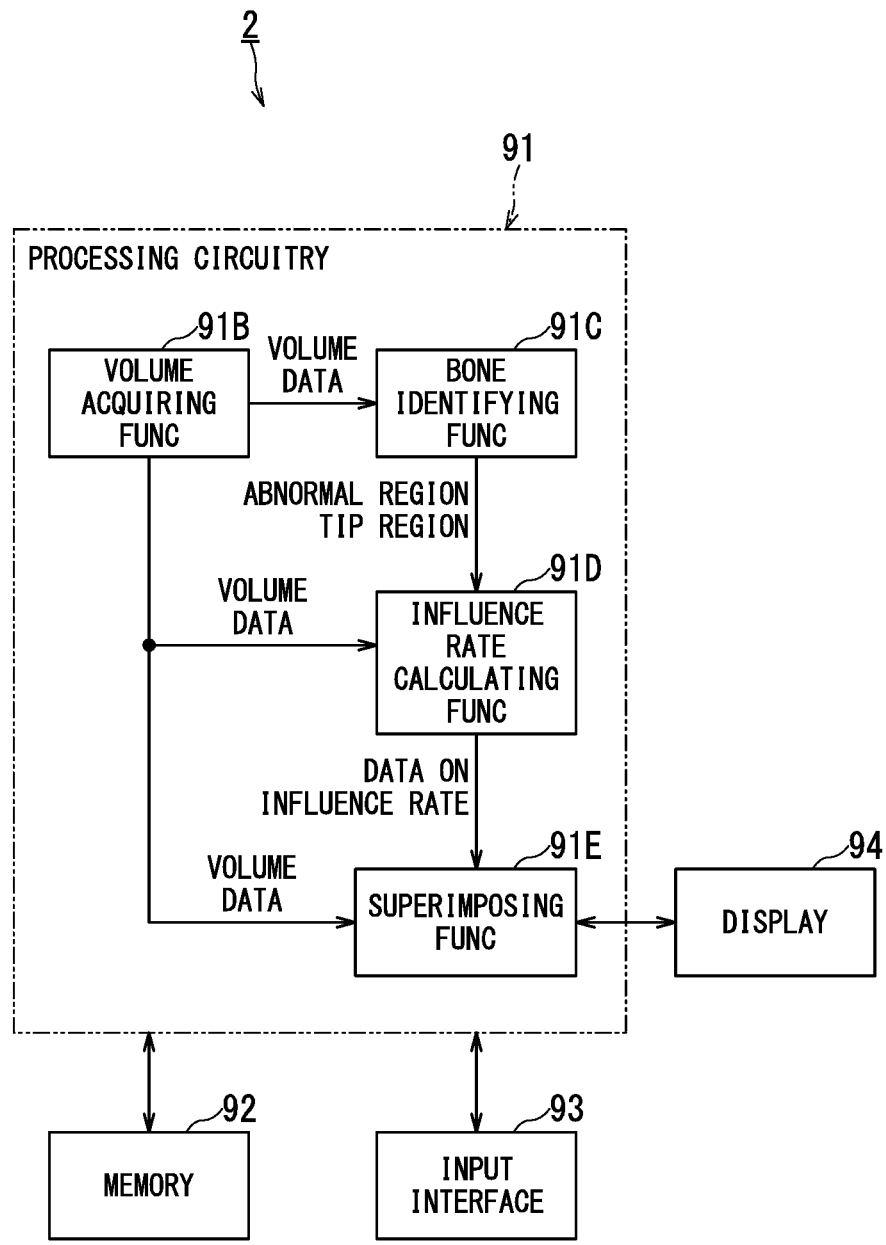
FIG. 12 is a block diagram showing functions of the medical image processing apparatus according to the embodiment.

FIG. 12 is a block diagram showing functions of the medical image processing apparatus.

When the processing circuitry 91 executes a program, the medical image processing apparatus 2 achieves a volume acquiring function (volume acquiring unit) 91B, a bone identifying function (bone identifying unit) 91C, an influence rate calculating function (influence rate calculating unit) 91D, and a superimposing function (superimposing unit) 91E. All or part of the functions 91B to 91E may be installed as the hardware included in the medical image processing apparatus 12.

The volume acquiring function 91B includes a function of acquiring medical volume data including bones and an organ from the memory 91 or an external device via the network. It should be noted that the volume acquiring function 91B may include a function of acquiring multiple tomographic images from the memory 91 or an external device via the network, performing interpolation processing as needed based on the multiple tomographic images, and generating medical volume data including the bones and the organ.

The bone identifying function 91C includes a function equivalent to that of the bone identifying function 81C shown in FIG. 2. The influence rate calculating function 91D includes a function equivalent to that of the influence rate calculating function 81D shown in FIG. 2. The superimposing function 91E includes a function equivalent to that of the superimposing function 81E shown in FIG. 2.

Figure 13:
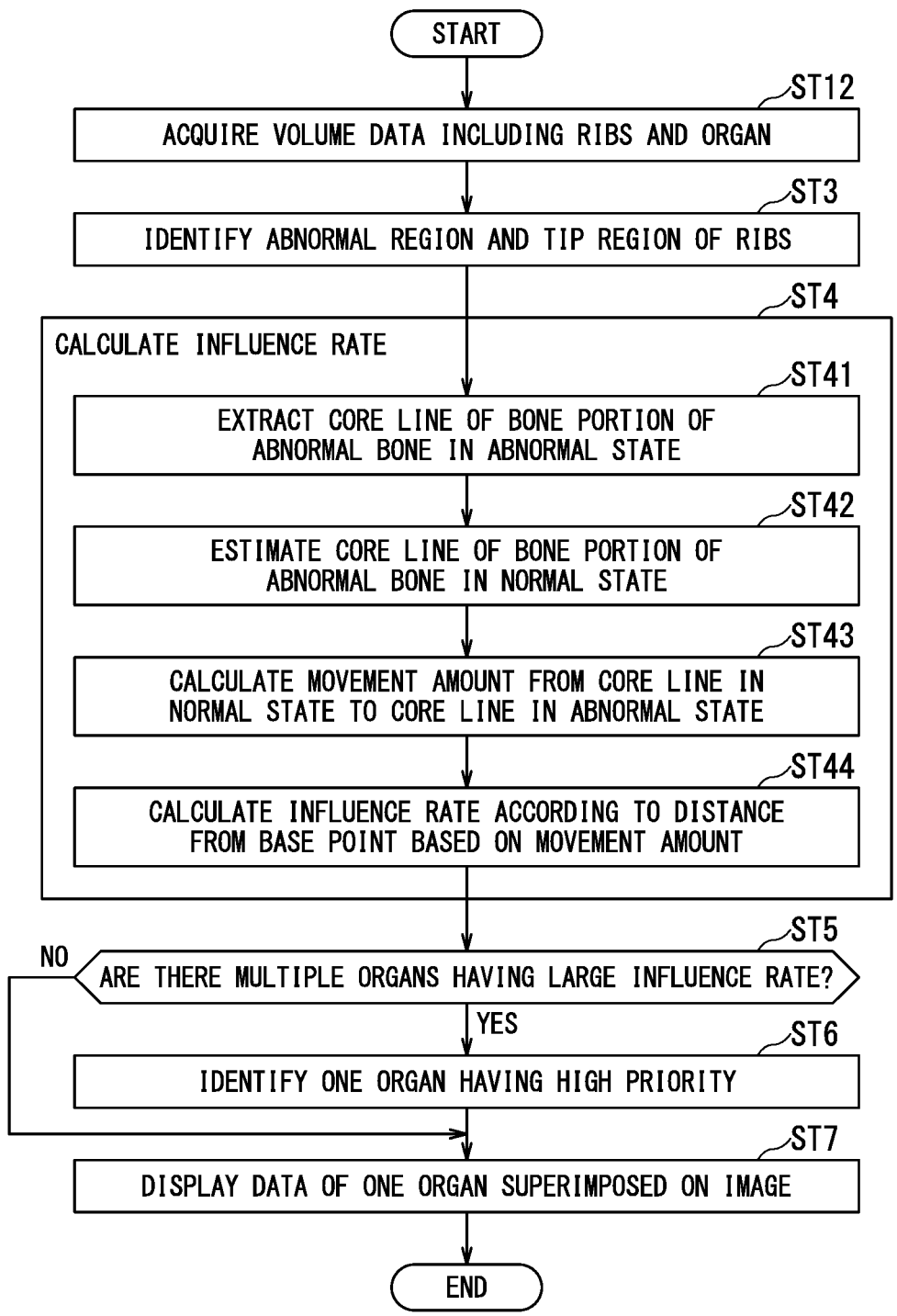
FIG. 13 is a flowchart showing an operation example of the medical image processing apparatus according to the embodiment.

FIG. 13 is a flowchart showing an operation example of the medical image processing apparatus 2.

The volume acquiring function 91B acquires volume data including ribs and an organ from the external circuit via the memory 91 or the network (step ST12). The bone identifying function 91C identifies, based on the volume data acquired in step ST12, an abnormal region and a tip region of an abnormal bone of the ribs (step ST3).

It should be noted that the same steps as those shown in FIG. 3 are denoted by the same reference numerals in FIG. 13, and the description thereof is omitted.

As described above, according to the medical image processing apparatus 2, it is possible to present to the operator the influence rate on the organ by the crack C or the tip portion E of the abnormal bone.

3. Effect

According to the at least one embodiment described above, it is possible to present the operator with the display of the organ according to the influence rate by the abnormal bone.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image diagnostic apparatus, comprising processing circuitry configured to:
    generate medical volume data including bones and an organ;
    identify, based on the volume data, the organ and an abnormal bone having an abnormal region of the bones;
    calculate, based on the organ and the abnormal bone of the volume data, an influence rate on the organ by the abnormal bone; and
    superimpose data indicating the influence rate on an image based on the volume data, thereby displaying the superimposed image on a display.

2. The medical image diagnostic apparatus according to claim 1, wherein
    the processing circuitry is configured to calculate a distance between the abnormal bone and the organ, and calculates, based on the distance, the influence rate.

3. The medical image diagnostic apparatus according to claim 2, wherein
    the processing circuitry is configured to
        calculate a movement amount from a normal position of the abnormal bone to a position of the identified abnormal bone, and
        set, based on the movement amount, a base point on the identified abnormal bone, and
        calculate the influence rate according to the distance between the base point and the organ.

4. The medical image diagnostic apparatus according to claim 3, wherein
    the processing circuitry is configured to estimate, based on positions of normal bones other than the abnormal bone, a position of the abnormal bone in a normal state.

5. The medical image diagnostic apparatus according to claim 4, wherein
    the processing circuitry is configured to estimate the position of the abnormal bone in the normal state by estimating, based on positions of core lines of the normal bones, a position of a core line of the abnormal bone.

6. The medical image diagnostic apparatus according to claim 3, wherein
    the processing circuitry is configured to
        calculate a vector from each position of a core line of the abnormal bone in a normal state, to a core line of the identified abnormal bone,
        set an end point of a vector having a maximum length as the base point.

7. The medical image diagnostic apparatus according to claim 6, wherein
    the processing circuitry is configured to superimpose the data on the influence rate on the image related to a multi-planar reconstruction (MPR) cross-section including the vector having the maximum length and orthogonal line thereof, thereby displaying the superimposed image on the display.

8. The medical image diagnostic apparatus according to claim 6, wherein
    the processing circuitry is configured to
        calculate vectors for volume data sets relating to time phases, respectively, and
        calculate the influence rate by using a volume data set including a vector having a maximum length.

9. The medical image diagnostic apparatus according to claim 8, wherein
    the processing circuitry is configured to
        set, as the base point, a vector having the maximum length for each of the volume data sets relating to the time phases, and
        calculate the influence rate according to the distance and an amount of change, the distance being calculated using one of the volume data sets, and the amount of change relating to a change with time of a length of a vector having the maximum length with respect to the base point.

10. The medical image diagnostic apparatus according to claim 3, wherein
    the processing circuitry is configured to calculate the influence rate according to, in addition to the distance, a distance between the base point and the abnormal region or a tip region of the abnormal bone.

11. The medical image diagnostic apparatus according to claim 3, wherein
    the processing circuitry is configured to calculate the influence rate according to, in addition to the distance, a type of the organ.

12. The medical image diagnostic apparatus according to claim 1, wherein
    the processing circuitry is configured to
        identify, based on the volume data, a tip region of the abnormal bone, and
        calculate, as the influence rate, an influence rate on the organ by the abnormal region or the tip region, based on the abnormal region and the tip region in the volume data.

13. The medical image diagnostic apparatus according to claim 1, wherein
the processing circuitry is configured to
calculate a movement amount from a normal position of the abnormal bone to a position of the identified abnormal bone,
estimate an impact rate on the organ by the abnormal bone, based on a bone density estimated based on the volume data and the movement amount, and
display the impact rate on the organ on the display.

14. A medical image processing apparatus, comprising processing circuitry configured to:
identify, based on volume data including bones and an organ, the organ and an abnormal bone having an abnormal region of the bones;
calculate, based on the organ and the abnormal bone of the volume data, an influence rate on the organ by the abnormal bone; and
superimpose data indicating the influence rate on an image based on the volume data, thereby displaying the superimposed image on a display.

15. A non-transitory computer readable medium on which a medical image processing program has been stored, the program configured to steps of:
identifying, based on volume data including bones and an organ, the organ and an abnormal bone having an abnormal region of the bones;
calculating, based on the organ and the abnormal bone of the volume data, an influence rate on the organ by the abnormal bone; and
superimposing data indicating the influence rate on an image based on the volume data, thereby displaying the superimposed image on a display.

* * * * *